United States Patent
Gao

(10) Patent No.: US 11,719,961 B1
(45) Date of Patent: Aug. 8, 2023

(54) METHOD OF CONTROLLING SHADE OF LIGHT VALVE FOR AUTO DARKENING FILTER

(71) Applicant: CHANGZHOU SHINE SCIENCE & TECHNOLOGY CO. LTD., Changzhou (CN)

(72) Inventor: Weiren Gao, Changzhou (CN)

(73) Assignee: CHANGZHOU SHINE SCIENCE & TECHNOLOGY CO. LTD., Jiangsu (CN)

( * ) Notice: Subject to any disclaimer, the term of this patent is extended or adjusted under 35 U.S.C. 154(b) by 0 days.

(21) Appl. No.: 17/985,772

(22) Filed: Nov. 11, 2022

Related U.S. Application Data

(63) Continuation of application No. PCT/CN2022/111086, filed on Aug. 9, 2022.

(30) Foreign Application Priority Data

Mar. 14, 2022 (CN) .......................... 202210244969.8

(51) Int. Cl.
  *G02C 7/10* (2006.01)
  *A61F 9/06* (2006.01)
  *G02C 7/08* (2006.01)

(52) U.S. Cl.
  CPC .............. *G02C 7/101* (2013.01); *A61F 9/065* (2013.01); *A61F 9/067* (2013.01); *G02C 7/083* (2013.01)

(58) Field of Classification Search
  CPC ......... G02C 7/083; G02C 7/101; A61F 9/065; A61F 9/067
  See application file for complete search history.

(56) References Cited

U.S. PATENT DOCUMENTS

| | | | |
|---|---|---|---|
| 5,248,880 | A | 9/1993 | Fergason |
| 2014/0320771 | A1 | 10/2014 | Keller et al. |
| 2015/0135389 | A1 | 5/2015 | Yang |
| 2022/0378617 | A1* | 12/2022 | Qu .......................... A61F 9/067 |

FOREIGN PATENT DOCUMENTS

| | | |
|---|---|---|
| CN | 201139682 Y | 10/2008 |
| CN | 101820837 A | 9/2010 |
| CN | 204169982 U | 2/2015 |
| CN | 114305861 A | 4/2022 |

* cited by examiner

*Primary Examiner* — Dung T Nguyen
(74) *Attorney, Agent, or Firm* — SZDC Law P.C.

(57) ABSTRACT

A method of controlling shade of light valve for auto darkening filter includes: controlling the current shade of the light valve at a first shade, continuously detecting a welding arc signal until it is detected; controlling the first shade of the light valve to change to a target shade, and maintaining the target shade for welding work until the welding arc signal is interrupted; controlling the light valve to transition from the target shade to the first shade within a time period $T_2$, wherein at least one intermediate shade is passed during the transition. For the conventional ADF, after the welding arc signal disappears, the control circuit immediately switches the light valve from the target shade to the light state shade. The switch of the light valve from the target shade to the light state shade occurs instantaneously, therefore the user may feel dazzling, causing damage to vision.

8 Claims, 8 Drawing Sheets

METHOD OF CONTROLLING SHADE OF LIGHT VALVE FOR AUTO DARKENING FILTER

This application is a Continuation Application of PCT/CN2022/111086, filed on Aug. 9, 2022, which claims priority to Chinese Patent Application No. 202210244969.8, filed on Mar. 14, 2022, which is incorporated by reference for all purposes as if fully set forth herein.

TECHNICAL FIELD

The present invention relates to the field of welding masks for welders, in particular to a method of controlling shade of light valve for auto darkening filter.

BACKGROUND

Conventional auto darkening filter (hereinafter referred to as ADF) controls the change of the shade of the light valve according to the flow shown in FIG. 1 based on the detected welding arc signal, wherein the abscissa X designates the time, and the ordinate Y designates the value of the shade of the light valve, which value is obtained according to blackness/transmittance of the ADF light valve.

Step A01: When the ADF is in the standby state, the light valve has a light state shade, usually #3 or #4, which is determined by the physical characteristics of the light valve;

Step A02: Upon detection of the welding arc signal, the control circuit controls the ADF to enter the normal operation and controls the light valve to maintain the value of the target shade, which value is set by the user;

Step A03: When the welding arc signal disappears, the control circuit controls the light valve to return to the light state, and the ADF returns to the standby state, waiting for the next welding arc signal.

In the above process, when the shade changes from high to low, that is, from the dark state to the light state, the transition occurs instantaneously and the magnitude of change is large, so the user's comfort is low and the degree of eye fatigue is high after a long period of work.

SUMMARY

The present invention provides a method of controlling shade of light valve for auto darkening filter, which can effectively solve the problems in the background art.

To this end, the present invention adopts technical solutions described below.

A method of controlling shade of light valve for auto darkening filter comprises the following steps:

controlling the current shade of the light valve at a first shade, continuously detecting a welding arc signal until it is detected;

controlling the first shade of the light valve to change to a target shade, and maintaining the target shade for welding work until the welding arc signal is interrupted;

controlling the light valve to transition from the target shade to the first shade within a time period $T_2$, wherein at least one intermediate shade is passed during the transition; and wherein the first shade is smaller than the target shade.

Further, during the transition of the light valve from the target shade to the first shade, the shade change process is a linear change process.

Further, during the transition of the light valve from the target shade to the first shade, the shade change process is a stepped change process.

Further, the method further comprises the following steps to cause the light valve to change from the first shade to the target shade after the welding arc signal is detected:

applying a high-voltage signal to the light valve and maintaining for a time period $T_0$, whereby the light valve obtains a second shade;

controlling the light valve to transition from the second shade to the target shade within a time period $T_1$, wherein at least one intermediate shade is passed during the transition; and wherein the target shade is between the first shade and the second shade, and the target shade is smaller than the highest shade of the light valve.

Further, the intermediate shade includes at least the highest shade of the light valve.

Further, the highest shade is maintained for a time period $T_{11}$, the light valve transitions from the highest shade to the target shade in a time period $T_{12}$, and the shade change process is a linear change process;

wherein $T_{12}=T_1-T_{11}$.

Further, the highest shade is maintained for a time period $T_{11}$, the light valve transitions from the highest shade to the target shade in a time period $T_{12}$, and the shade change process is a stepped change process;

wherein $T_{12}=T_1-T_{11}$.

Further, the time period $T_{12}$ is longer than the time period $T_{11}$.

A method of controlling shade of light valve for auto darkening filter comprises the following steps:

controlling the current shade of the light valve at a first shade, continuously detecting a welding arc signal until it is detected;

applying a high voltage signal to the light valve and maintaining for a time period $T_0$, whereby the light valve obtains a second shade;

controlling the light valve to transition from the second shade to the target shade within a time period $T_1$, wherein at least one intermediate shade is passed during the transition, and wherein the target shade is between the first shade and the second shade, and the target shade is smaller than the highest shade of the light valve; and maintaining the target shade for welding work.

Further, the high voltage signal is a positive voltage.

Further, the high voltage signal is a negative voltage.

With the technical solutions of the present invention, the following technical effects can be achieved.

For the conventional ADF, after the welding arc signal disappears, the control circuit immediately switches the light valve from the target shade to the light state shade. If the user is welding with high current, even after the welding arc ends, the welded workpiece will still have a hot welding pool. The switch of the light valve from the target shade to the light state shade occurs instantaneously, therefore the user may feel dazzling, causing damage to vision. Through the technical solution according to the present invention, the visual transition is provided with a delay time, thereby effectively improving the comfort of the user.

In addition, for the conventional ADF, after application of the high voltage to the light valve, the control circuit directly switches the light valve to the target shade. In this case, if the target shade is too low, the user will suffer visual discomfort, because the shade changes significantly in a very short period of time, the user will first experience a very dark environment due to the presence of the high voltage signal, and then immediately jump to a lighter state through the change of the shade. The user will mistakenly think that he is "punched" by the welding arc light. Through the present invention, the transition between the extremely dark environment and the target shade can be obtained, so that the user can make it clear that the change in the degree of light and darkness of the environment does not come from the arc light, and can obtain the time to adapt to the change in light and darkness, so as to obtain a better use experience.

DESCRIPTION OF THE DRAWINGS

In order to more clearly illustrate the embodiments of the present invention or the technical solutions in the prior art, the accompanying drawings to be used in the description of the embodiments or prior art will be briefly described below. It is obvious that the accompanying drawings in the following description are only some of the embodiments recorded in the present invention, and other accompanying drawings can be obtained according to these accompanying drawings without creative work for those of ordinary skill in the art.

DETAILED DESCRIPTION

The technical solutions in the embodiments of the present invention will be described clearly and completely in conjunction with the accompanying drawings in the embodiments of the present invention. Obviously, the described embodiments are only a part of the embodiments of the present invention, rather than all the embodiments.

Unless otherwise defined, all technical and scientific terms used herein have the same meaning as commonly understood by those skilled in the art of the present invention. The terms used herein are for the purpose of describing specific embodiments only and are not intended to limit the invention. The term "and/or" as used herein includes any and all combinations of one or more of the related listed items.

Embodiment 1

Figure 1:
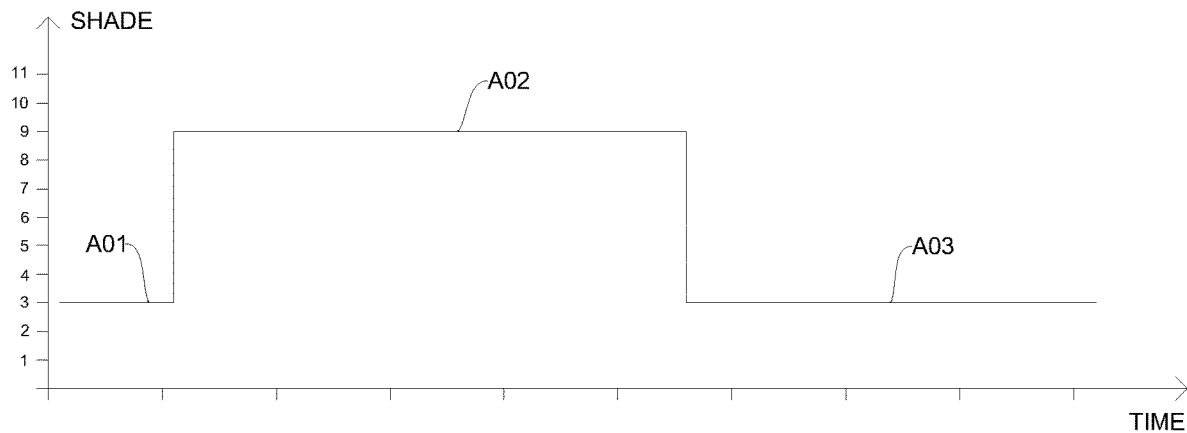
FIG. 1 illustrates the control flow of the light valve shade for the conventional ADF described in the background art in a time-shade coordinate system.
Figure 2:
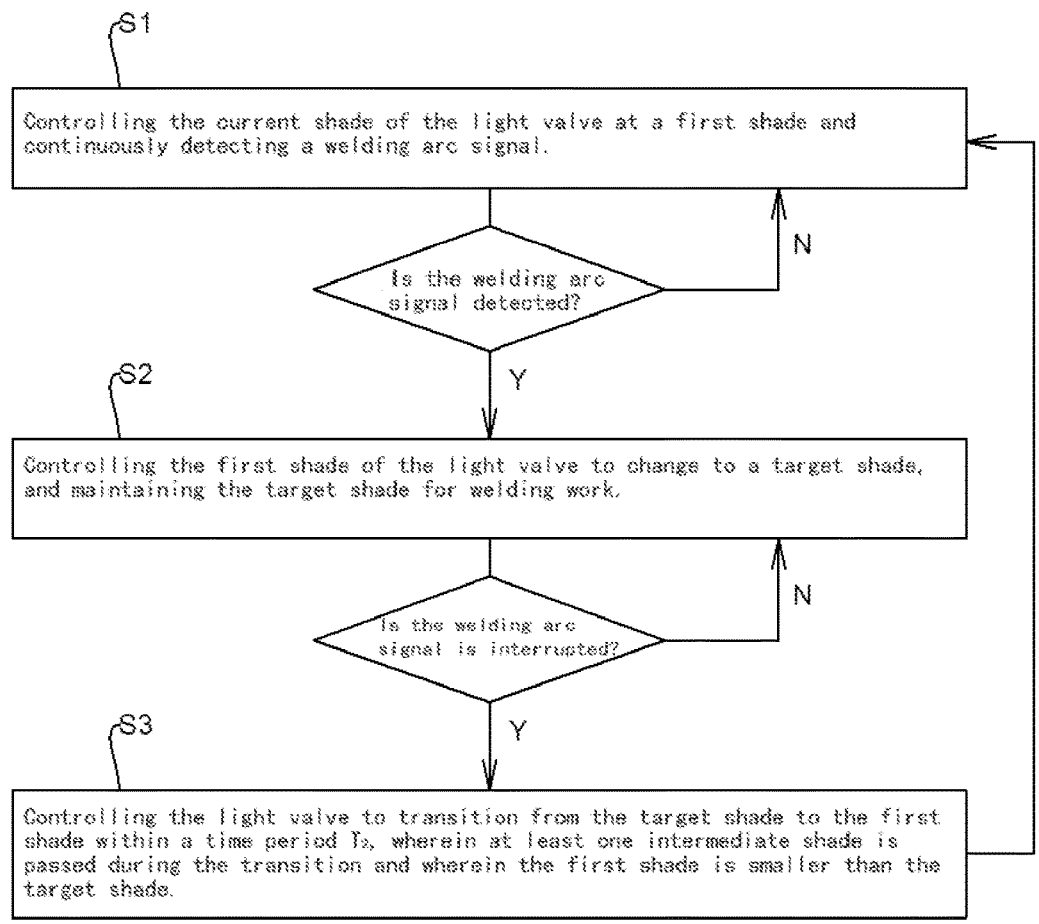
FIG. 2 illustrates the control flow of the light valve shade for ADF in Embodiment 1.
Figure 3:
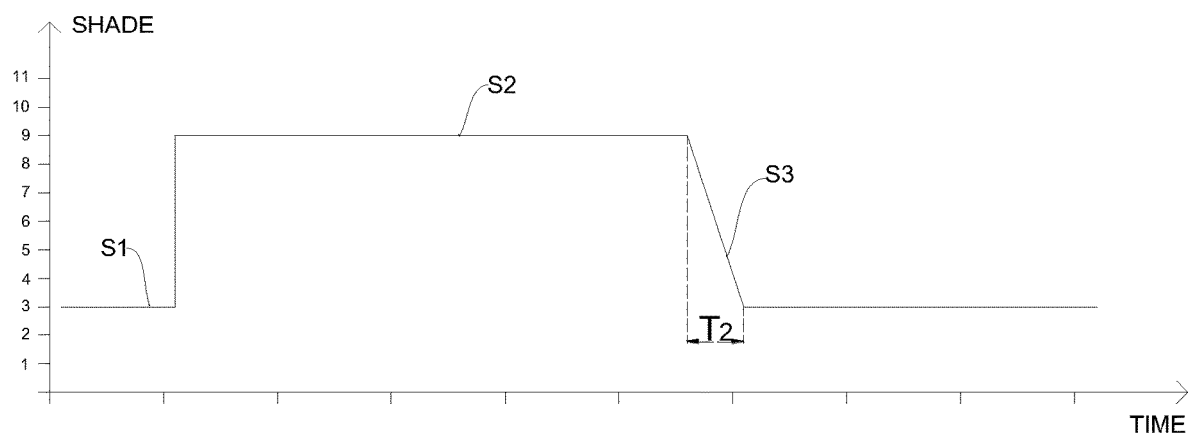
FIG. 3 illustrates the control flow in FIG. 2 in a time-shade coordinate system, wherein the transition in step S3 is a linear transition.
Figure 4:
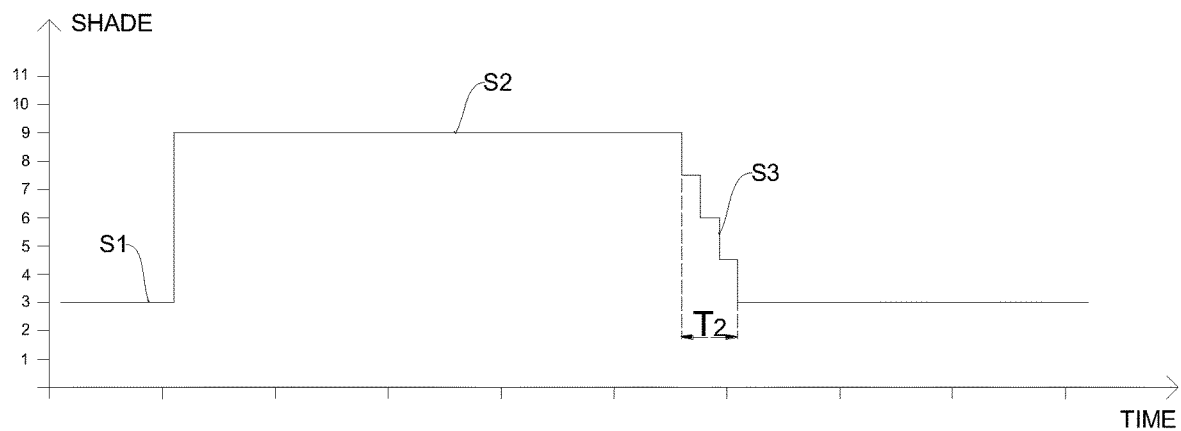
FIG. 4 illustrates the control flow in FIG. 2 in a time-shade coordinate system, wherein the transition in step S3 is a stepped transition.

As shown in FIG. 1, a method of controlling shade of light valve for auto darkening filter comprises the following steps:

S1: controlling the current shade of the light valve at a first shade, at this time the ADF is in standby mode, the light valve has a light state shade, usually #3 or #4, or other values and, as shown in FIGS. 3 and 4, #3 is used as the first shade in this embodiment; and continuously detecting a welding arc signal until it is detected;

S2: controlling the first shade of the light valve to change to a target shade, and maintaining the target shade for welding work until the welding arc signal is interrupted;

S3: controlling the light valve to transition from the target shade to the first shade within a time period $T_2$, at which time the ADF starts delay time to control the light valve to return to the light state and returns to the standby state, wherein at least one intermediate shade is passed during the transition so as to protect the user's eyes and improve the welding comfort, and wherein the first shade is smaller than the target shade.

After the end of step S3, the methods return to step S1 again, waiting for the next welding arc signal. The delay time $T_2$ is adjustable in a range from several microseconds to several seconds. The user may set the delay time $T_2$ according to conditions such as the type of workpieces to be welded, the magnitude of welding current, the residual welding temperature, etc.

Through this embodiment, the following problems are effectively solved.

For the conventional ADF, after the welding arc signal disappears, the control circuit immediately switches the light valve from the target shade to the light state shade. If the user is welding with high current, even after the welding arc ends, the welded workpiece will still have a hot welding pool. The switch of the light valve from the target shade to the light state shade occurs instantaneously, therefore the user may feel dazzling, causing damage to vision. Through the technical solution according to the present invention, the visual transition is provided with a delay time, thereby effectively improving the comfort of the user.

As a preferred embodiment, during the transition of the light valve from the target shade to the first shade, the shade change process is a linear change process, as shown in FIG. 3, so that the visual transition is smoother. Alternatively, during the transition of the light valve from the target shade to the first shade, the shade change process is a stepped change process, as shown in FIG. 4. In this way, although the change of shade is less smooth than the preferred embodiment, it also has its own advantages—the stepped transition provides the transition between adjacent shades with a pause, offering the user a short time for judging the welded items, so that better control of the welding process is achieved when the user distinguishes the change of the welded items from the change of the shades through such short pause.

Embodiment 2

Figure 5:
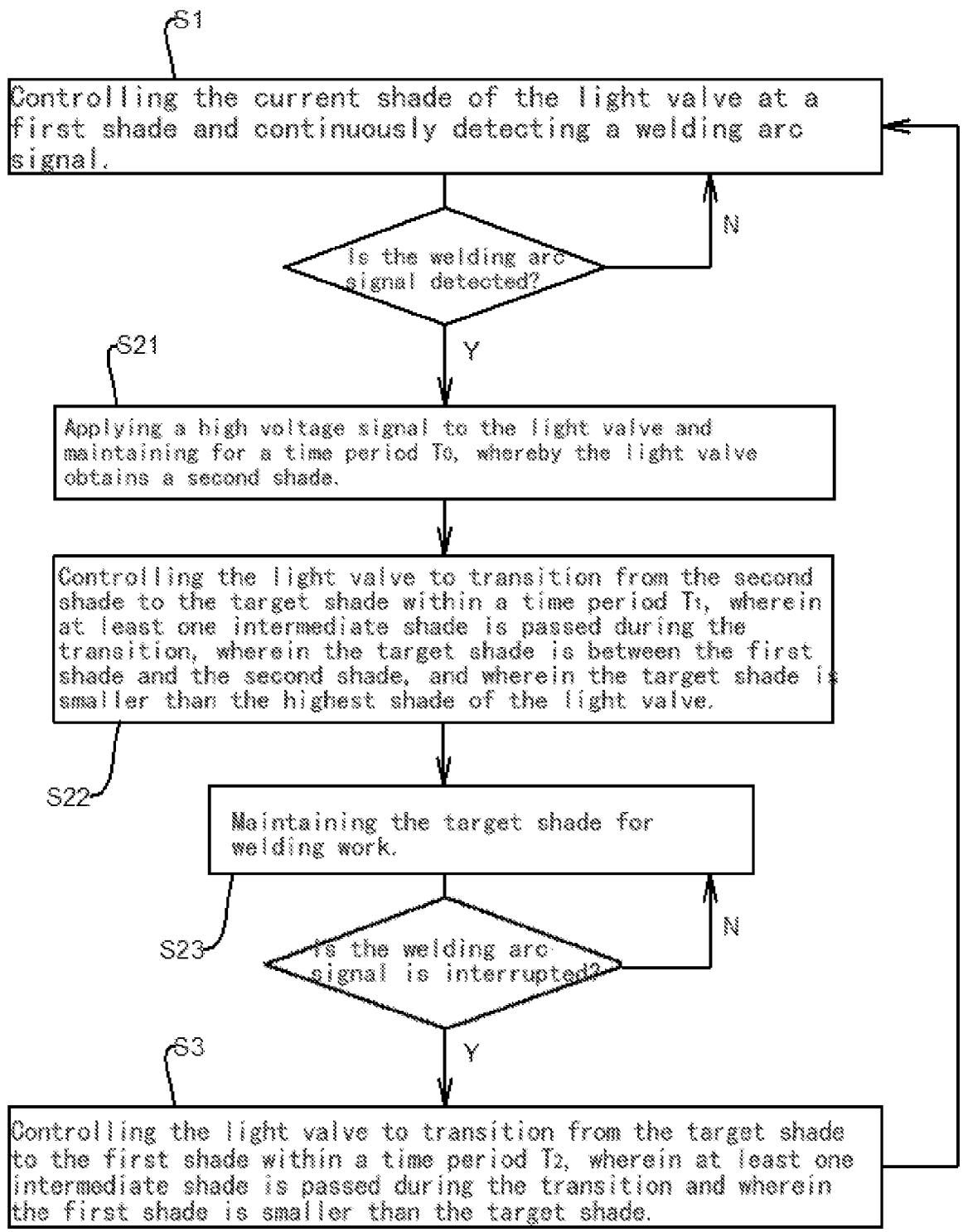
FIG. 5 is illustrates the control flow of the light valve shade for ADF in Embodiment 2.

As shown in FIG. 5, a method of controlling shade of light valve for auto darkening filter comprises the following steps:

S1: controlling the current shade of the light valve at a first shade, at this time the ADF is in standby mode, the light valve has a light state shade, usually #3 or #4, or other values and, as shown in FIGS. 3 and 4, #3 is used as the first shade in this embodiment; and continuously detecting a welding arc signal until it is detected;

S21: applying a high voltage signal to the light valve and maintaining for a time period $T_0$, whereby the light valve obtains a second shade, wherein the time period $T_0$ is adjustable in a range from several microseconds to several seconds; in this step, the application of the high voltage signal greatly increases the start-up speed of the light valve, so that it only takes 50 microseconds from the detection of the welding arc to the darkening of the light valve in the presence of the high voltage signal and, in contrast, this process may take 2 milliseconds in the absence of high voltage signal, such difference in time consumption makes the user experience greatly different; the second shade obtained in this step will be higher than the highest shade of the light valve that is determined by the control circuit and the physical characteristics of the light valve, and as shown in FIGS. 6-9, the second shade is #17;

S22: controlling the light valve to transition from the second shade to the target shade within a time period $T_1$, wherein at least one intermediate shade is passed during the transition, wherein the time period $T_1$ is adjustable in a range from several microseconds to several seconds, and wherein the target shade is between the first shade and the second shade, and the target shade is smaller than the highest shade of the light valve; similarly, this gradual change protects the user's eyes and improves the welding comfort;

S23: maintaining the target shade for welding work until the welding arc signal is interrupted; and S3: controlling the light valve to transition from the target shade to the first shade within a time period $T_2$, at which time the ADF starts delay time to control the light valve to return to the light state and returns to the standby state, wherein at least one intermediate shade is passed during the transition so as to protect the user's eyes and improve the welding comfort, and wherein the first shade is smaller than the target shade.

After the end of step S3, the methods return to step S1 again, waiting for the next welding arc signal. In this embodiment, the delay time $T_2$ is adjustable in a range from several microseconds to several seconds. The user may set the delay time $T_2$ according to conditions such as the type of workpieces to be welded, the magnitude of welding current, the residual welding temperature, etc.

Through this embodiment, in addition to the technical problems solved in Embodiment 1, the following problems are solved.

In addition, for the conventional ADF, after application of the high voltage to the light valve, the control circuit directly switches the light valve to the target shade. Of course, the specific target shade is set by the user, and FIGS. 6-9 show the solution in which the target shade is #9. In this case, if the target shade is too low, the user will suffer visual discomfort, because a change of more than 10 shades may happen in a very short period of time, the user will first experience a very dark environment due to the presence of the high voltage signal, and then immediately jump to a lighter state through the change of the shade. The user will mistakenly think that he is "punched" by the welding arc light. Through this embodiment, the transition between the extremely dark environment and the target shade can be obtained, so that the user can make it clear that the change in the degree of light and darkness of the environment does not come from the arc light, and can obtain the time to adapt to the change in light and darkness, so as to obtain a better use experience.

Figure 6:
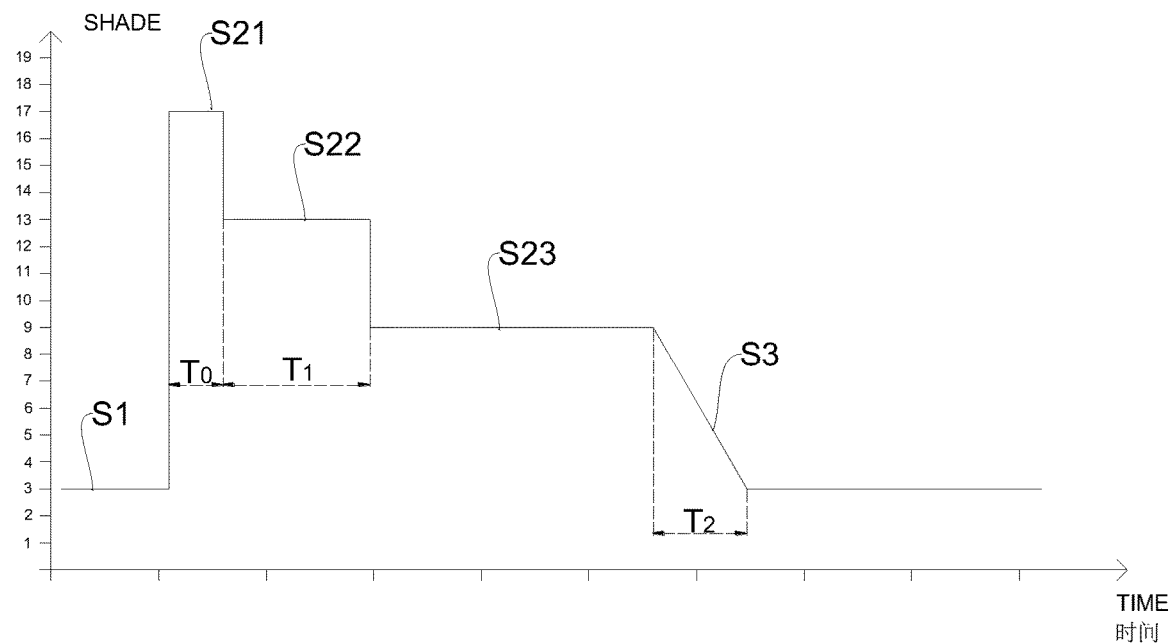
FIG. 6 illustrates the control flow in FIG. 5 in a time-shade coordinate system, wherein the intermediate shade in step S22 includes only the highest shade and the transition in step S3 is a linear transition.

As a preferred embodiment, the intermediate shade at least includes the highest shade of the light valve, usually in the range of #11-#16. FIG. 6 shows the case where the intermediate shade only includes the highest shade of the light valve and the highest shade lasts for a time period $T_1$. By controlling the light valve at the highest shade, the light valve returns to normal operation after the high voltage signal ends, wherein the time period $T_1$ is adjustable in a range from several microseconds to several seconds.

Figure 7:
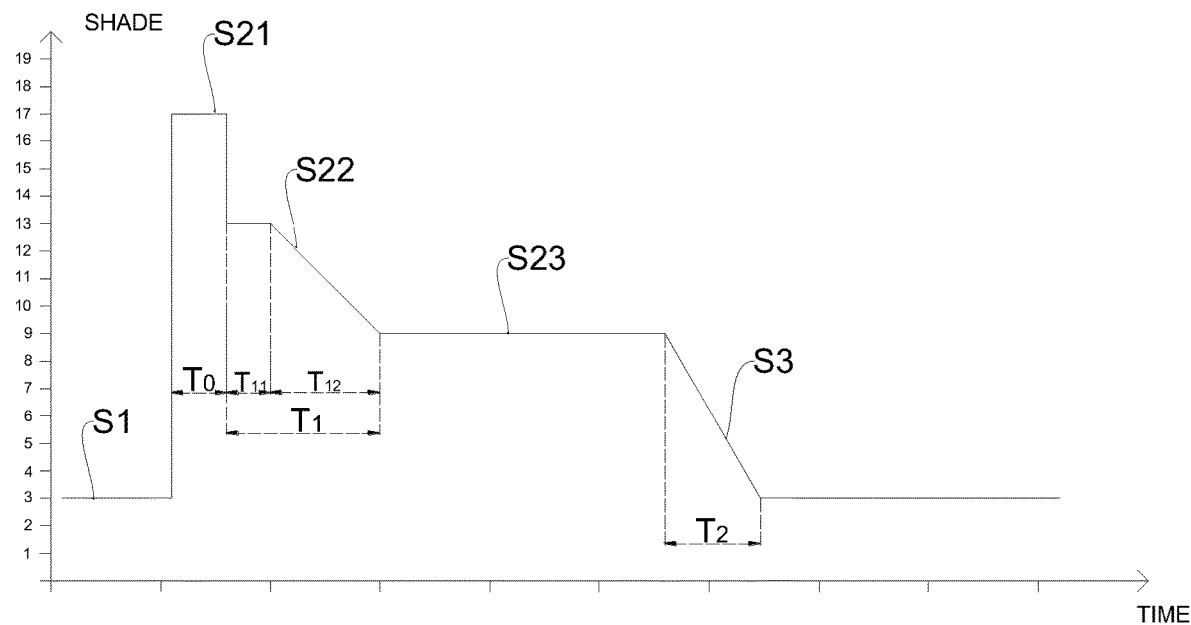
FIG. 7 illustrates the control flow in FIG. 5 in a time-shade coordinate system, wherein the intermediate shade in step S22 includes both the highest shade and the target shade transitioned from the highest shade by a linear transition, and wherein the transition in step S3 is a linear transition.

Of course, in addition to the case where the intermediate shade only includes the highest shade, other intermediate shades can also be included in the process of transitioning from the second shade to the target shade. As shown in FIG. 7, the highest shade is maintained for a time period $T_{11}$, and the light valve transitions from the highest shade to the target shade in the time period $T_{12}$, the shade change process is a linear change process, wherein $T_{12}=T_1-T_{11}$. In this way, the visual transition is made smoother, and by maximizing the difference between the highest shade and the target shade, the user can obtain the maximum adaptation space.

Figure 8:
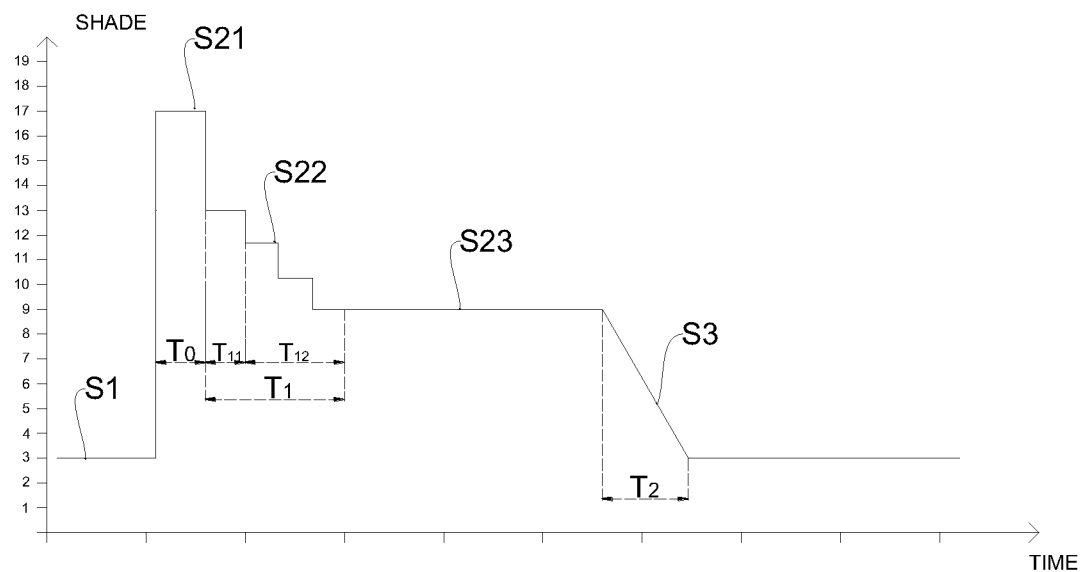
FIG. 8 illustrates the control flow in FIG. 5 in a time-shade coordinate system, wherein the intermediate shade in step S22 includes both the highest shade and the target shade transitioned from the highest shade by a stepped transition, and wherein the transition in step S3 is a linear transition.

Alternatively, as shown in FIG. 8, the highest shade is maintained for a time period $T_{11}$, so that the user can adapt to the highest shade within this time period and the light valve can also be stabilized. The light valve transitions from the highest shade to the target shade in the time period $T_{12}$, and the shade change process is a stepped change process, wherein $T_{12}=T_1-T_{11}$. In this way, although the change of shade is less smooth than the preferred embodiment, the stepped transition provides the transition between adjacent shades with a pause, offering the user a short time for judging the welded arc.

In this embodiment, it is preferable that the time period $T_{12}$ is longer than the time period $T_{11}$, so that after both the operator and the light valve transition through the highest shade, more time for transitioning from the highest shade to the target shade can be obtained, thereby achieving better user experience.

Figure 9:
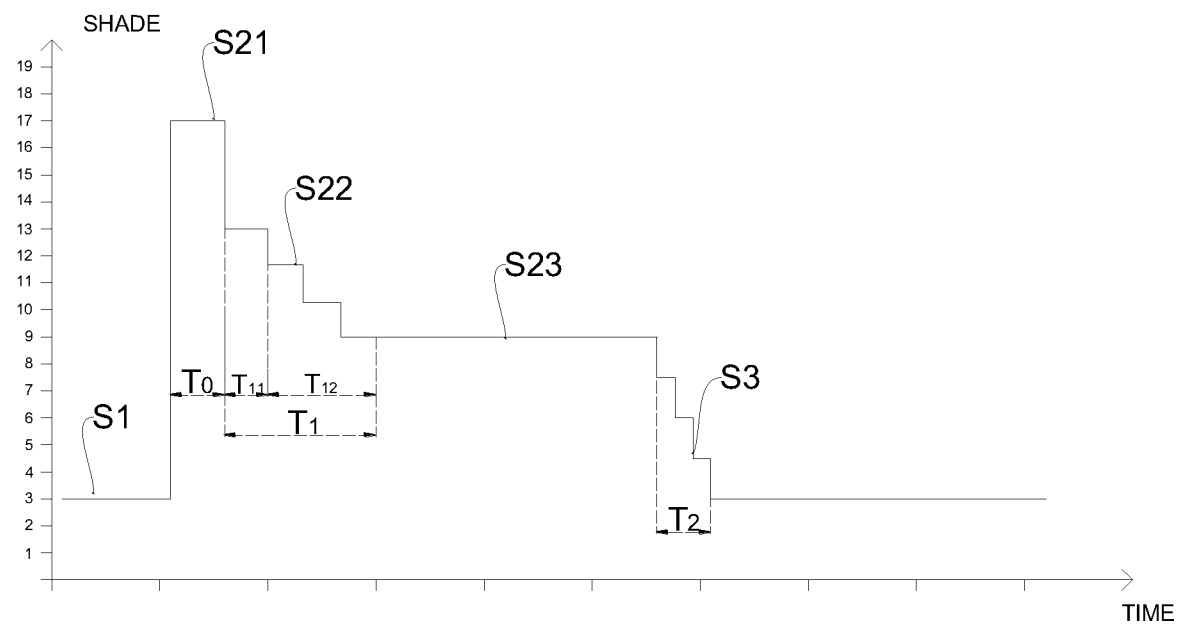
FIG. 9 illustrates the control flow in FIG. 5 in a time-shade coordinate system, wherein the intermediate shade in step S22 includes both the highest shade and the target shade transitioned from the highest shade by a stepped transition, and wherein the transition in step S3 is a stepped transition.

FIG. 7 shows an embodiment of the transition of the light valve from the highest shade to the target shade, for which the shade change process is a linear change process, and the transition of the light valve from the target shade to the first shade, for which the shade change process is a stepped change process, in the time period $T_{12}$. FIG. 8 shows an embodiment of the transition of the light valve from the highest shade to the target shade, for which the shade change process is a stepped change process, and the transition of the light valve from the target shade to the first shade, for which the shade change process is a linear change process, in the time period $T_{12}$. In addition to the above situations, the present invention also protects the alternative method in which the shade change process is a linear change process during the transition of the light valve from the target shade to the first shade, as shown in FIG. 9 which replaces FIG. 8.

Embodiment 3

Figure 10:
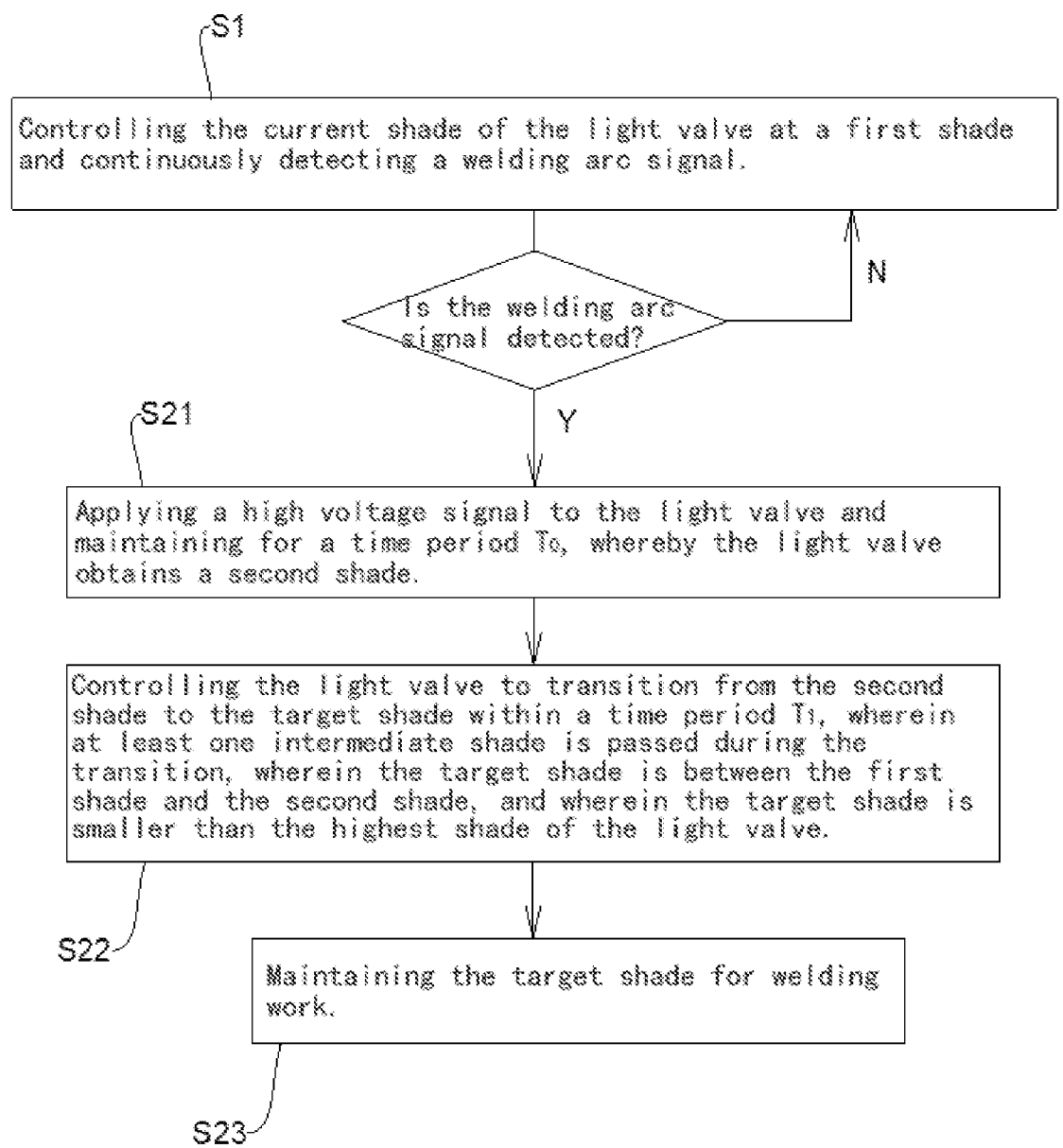
FIG. 10 illustrates the control flow of the light valve shade for ADF in Embodiment 3.
Figure 11:
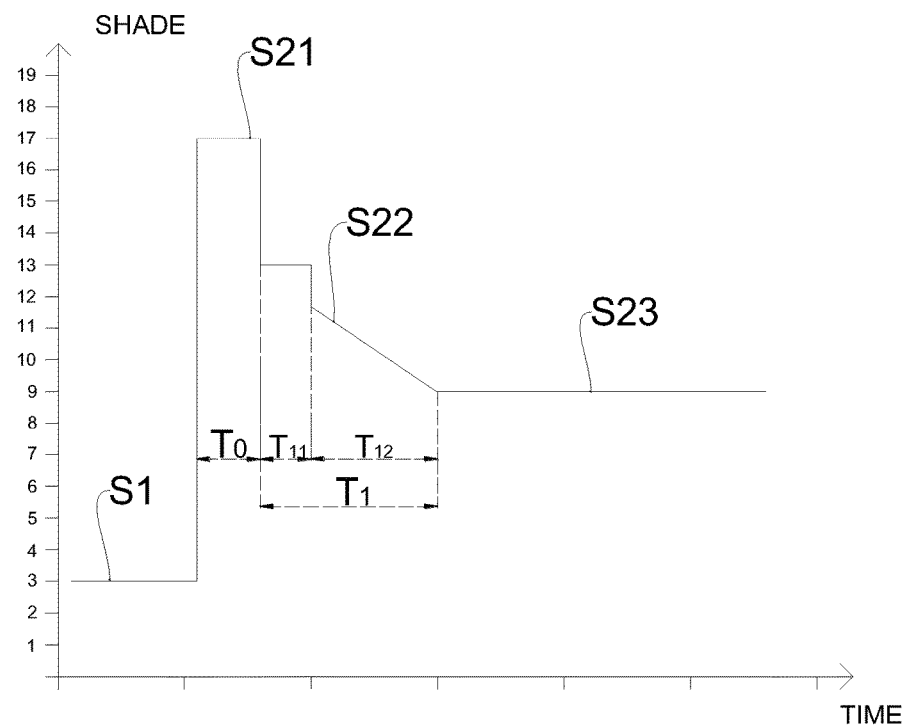
FIG. 11 illustrates the control flow in FIG. 10 in a time-shade coordinate system, wherein the intermediate shade in step S22 includes both the highest shade and the target shade transitioned from the highest shade by a linear transition.

As shown in FIGS. 10 and 11, a method of controlling shade of light valve for auto darkening filter comprises the following steps:

S1: controlling the current shade of the light valve at a first shade, continuously detecting a welding arc signal until it is detected;

S21: applying a high voltage signal to the light valve and maintaining for a time period $T_0$, whereby the light valve obtains a second shade;

S22: controlling the light valve to transition from the second shade to the target shade within a time period $T_1$, wherein at least one intermediate shade is passed during the transition, and wherein the target shade is between the first shade and the second shade, and the target shade is smaller than the highest shade of the light valve; and S23: maintaining the target shade for welding work.

Figure 12:
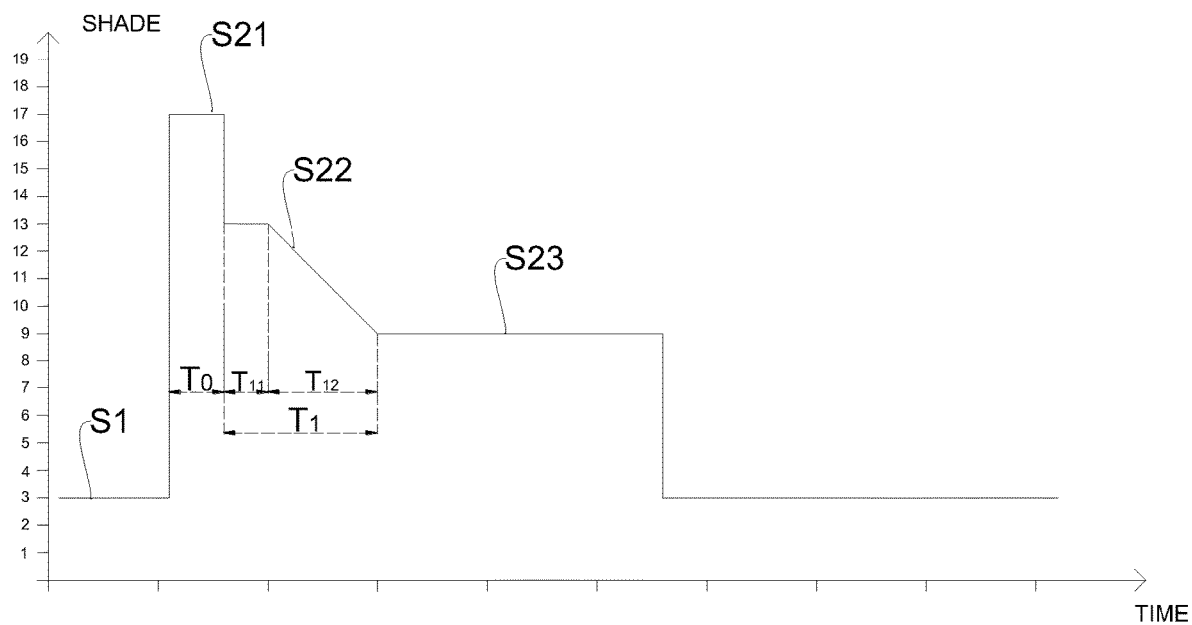
FIG. 12 illustrates the combination of the process in FIG. 11 and the conventional process of the control circuit directly controlling the light valve to return to the light state after the welding arc signal disappears.

In this embodiment, the technical purposes of steps S1 to S23 are the same as those in the Embodiment 2, the difference is that the above-described technical solution can be combined with a different mode of change from the target shade to the first shade to obtain a technical solution different from Embodiment 2. Such technical solution includes at least the method shown in FIG. 12, that is, when the welding arc signal disappears, the control circuit controls the light valve to return to the light state and the ADF returns to the standby state, waiting for the next welding arc signal. This method is especially suitable for the case where the numerical difference between the target shade and the first shade is small, and/or the area of the welding pool is small, in which case the rapid shade change has little impact on the user's comfort and can reduce the difficulty of control.

Figure 13:
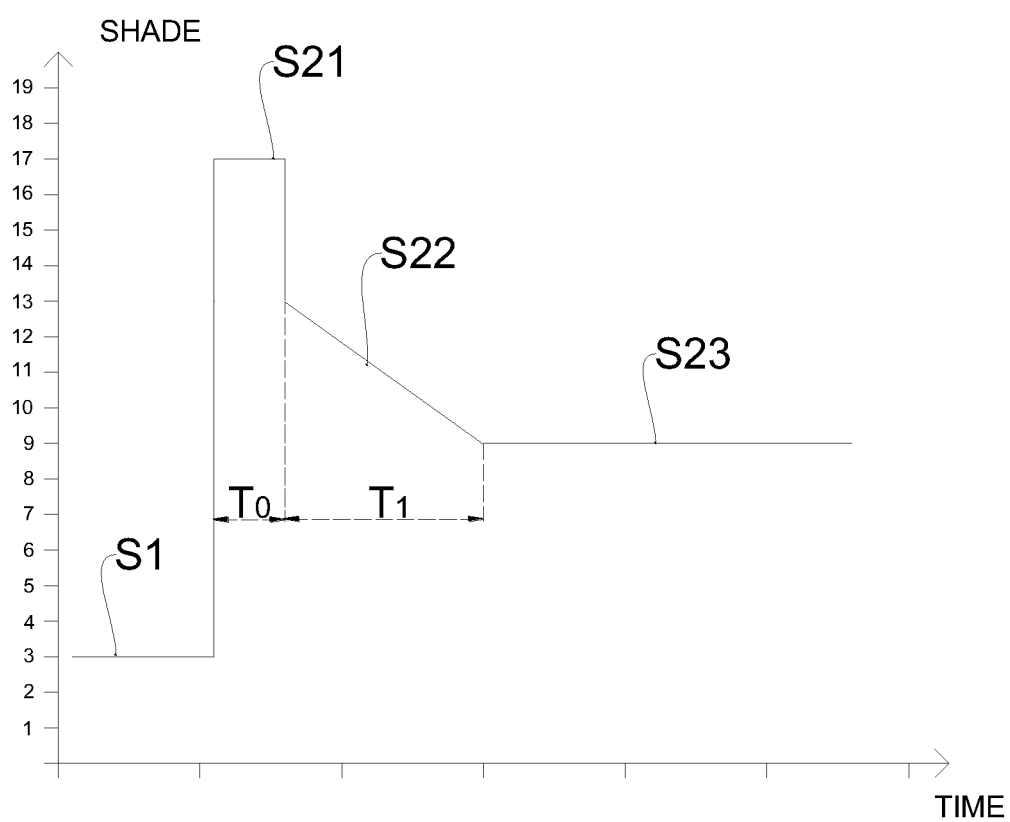
FIG. 13 illustrates the control flow in FIG. 10 in a time-shade coordinate system, wherein the step S22 only includes the process of linear transition from the highest shade to the target shade.

As a preferred embodiment, as shown in FIG. 13, the present invention also protects the technical solution of the direct transition from the highest shade to the target shade, that is, the highest shade does not last for a period of time, and in this case, both linear smooth transition and stepped transition are within the protection scope of the present invention.

As a preferred embodiment, the high voltage signal is a positive voltage or a negative voltage, and its application time is adjustable in a range from several microseconds to several seconds.

All the control technologies of the intelligent ADF according to the present invention can be achieved based on the single chip microcomputer (MCU) in the internal circuit. The performance of the product is greatly improved by the segmented shade control technology. The key parameters of each time period can be set by the manufacturer at the time of delivery, or can be reset by the user through knobs, buttons, remote controllers, mobile apps, computer software, etc., which are within the protection scope of the present invention.

The basic principles, main features and advantages of the present invention have been shown and described above. Those skilled in the industry should understand that the present invention is not limited by the foregoing embodiments. The foregoing embodiments and descriptions only illustrate the principles of the present invention. Without departing from the spirit and scope of the present invention, the present invention will have various changes and improvements, which fall within the scope of the claimed invention. The scope of protection claimed by the present invention is defined by the appended claims and their equivalents.

The invention claimed is:

1. A method of controlling a shade of a light valve for an auto darkening filter, comprising the following steps:
controlling a current shade of the light valve at a first shade, continuously detecting a welding arc signal until being detected; perform a next step;
controlling a first shade of the light valve to change to a target shade, wherein applying a high voltage signal to the light valve and maintaining for a time period $T_0$, whereby the light valve obtains a second shade;
controlling the light valve to transition from the second shade to the target shade within a time period $T_1$, wherein at least one intermediate shade is passed during the transition; and wherein the target shade is between the first shade and the second shade, and the target shade is smaller than the highest shade of the light valve, wherein the intermediate shade includes at least the highest shade of the light valve, wherein the highest shade is maintained for a time period $T_{11}$, the light valve transitions from the highest shade to the target shade in a time period $T_{12}$, and the shade change process is a linear change process;
wherein $T_{12}=T_1-T_{11}$
wherein $T_{12}>T_{11}$
and maintaining the target shade for welding work until the welding arc signal is interrupted; and
controlling the light valve to transition from the target shade to the first shade within a time period $T_2$, wherein at least one intermediate shade is passed during the transition;
wherein the first shade is smaller than the target shade.

2. The method of controlling shade of light valve for auto darkening filter according to claim 1, wherein during the transition of the light valve from the target shade to the first shade, the shade change process is a linear change process.

3. The method of controlling shade of light valve for auto darkening filter according to claim 1, wherein during the transition of the light valve from the target shade to the first shade, the shade change process is a stepped change process.

4. The method of controlling shade of light valve for auto darkening filter according to claim 1, wherein the high voltage signal is a positive voltage or a negative voltage.

5. A method of controlling a shade of a light valve for an auto darkening filter, comprising the following steps:
controlling a current shade of the light valve at a first shade, continuously detecting a welding arc signal until being detected; perform a next step;
controlling a first shade of the light valve to change to a target shade, wherein applying a high voltage signal to the light valve and maintaining for a time period $T_0$, whereby the light valve obtains a second shade;
controlling the light valve to transition from the second shade to the target shade within a time period $T_1$, wherein at least one intermediate shade is passed during the transition; and wherein the target shade is between the first shade and the second shade, and the target shade is smaller than the highest shade of the light valve, wherein the intermediate shade includes at least the highest shade of the light valve, wherein the highest shade is maintained for a time period $T_{11}$, the light valve transitions from the highest shade to the target shade in a time period $T_{12}$, and the shade change process is a stepped change process;

wherein $T_{12}=T_1-T_{11}$ wherein $T_{12}>T_{11}$ and maintaining the target shade for welding work until the welding arc signal is interrupted; and controlling the light valve to transition from the target shade to the first shade within a time period $T_2$, wherein at least one intermediate shade is passed during the transition;

wherein the first shade is smaller than the target shade.

6. The method of controlling shade of light valve for auto darkening filter according to claim 5, wherein during the transition of the light valve from the target shade to the first shade, the shade change process is a linear change process.

7. The method of controlling shade of light valve for auto darkening filter according to claim 5, wherein during the transition of the light valve from the target shade to the first shade, the shade change process is a stepped change process.

8. The method of controlling shade of light valve for auto darkening filter according to claim 5, wherein the high voltage signal is a positive voltage or a negative voltage.

* * * * *